United States Patent [19]

Berkovits

[11] Patent Number: 4,932,406

[45] Date of Patent: Jun. 12, 1990

[54] DUAL CHAMBER RATE RESPONSIVE PACEMAKER

[75] Inventor: Barouh V. Berkovits, Newton Highlands, Mass.

[73] Assignee: Medtronic, Minneapolis, Minn.

[21] Appl. No.: 249,046

[22] Filed: Sep. 23, 1988

[51] Int. Cl.$^5$ .............................................. A61B 1/00
[52] U.S. Cl. ............................................. 128/419 PG
[58] Field of Search ......... 128/419 P, 419 PG, 419 D

[56] References Cited

U.S. PATENT DOCUMENTS

| | | | |
|---|---|---|---|
| 4,485,818 | 12/1984 | Leckrone et al. | 128/419 PG |
| 4,527,568 | 7/1985 | Rickards | 128/419 PG |
| 4,572,841 | 1/1986 | Brockway et al. | 128/419 PG |
| 4,803,987 | 2/1989 | Calfee et al. | 128/419 PG |
| 4,817,606 | 4/1989 | Lekholm | 128/419 PG |
| 4,856,523 | 8/1989 | Shoulder | 128/419 PG |

OTHER PUBLICATIONS

Article "A Review of Pacemakers That Physiologically Increase Rate: The DDD and Rate-Responsive Pacemakers", by Fearnot et al., published in *Progress in Cardiovascular Diseases*, vol. XXIX, No. 2, 1986, pp. 145–164.

Article "Improved DDD Pacing with a New Rate Limiting Algorithm", by Barouh V. Berkovits, published in the *Proceedings of the 8th World Symposium on Cardiac Pacing and Electrophysiology*.

Article "A New Rate Limiting Algorithm Prevents Some A-V Reentrant Tachycardias", by Barouh V. Berkovits, published in *Progress in Clinical Pacing*, Rome, 1986.

*Primary Examiner*—Francis Jaworski
*Assistant Examiner*—George Manual
*Attorney, Agent, or Firm*—Reed A. Duthler; Joseph F. Breimayer; Robert C. Beck

[57] ABSTRACT

A pacemaker which operates in an atrial synchronized modality when the sensed atrial rate is within a physiologic range and which paces at a sensor determined rate when the atrial rate is above or below the physiologic range.

5 Claims, 5 Drawing Sheets

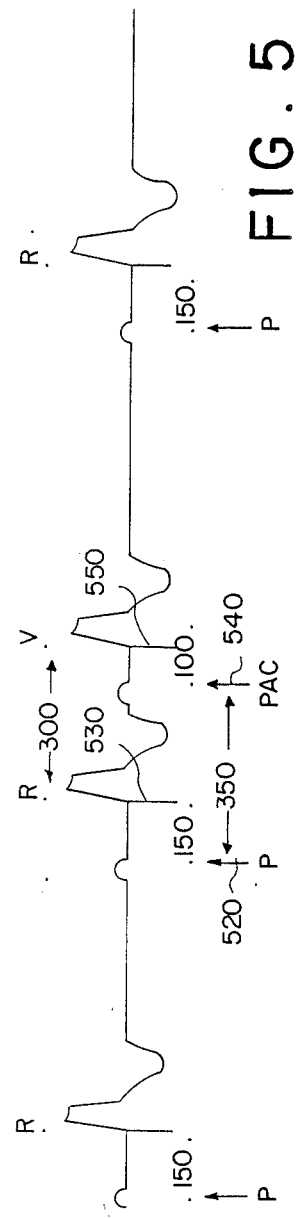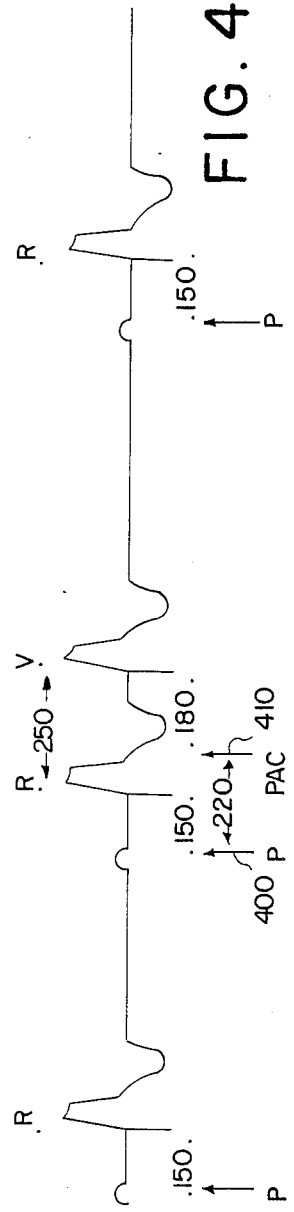

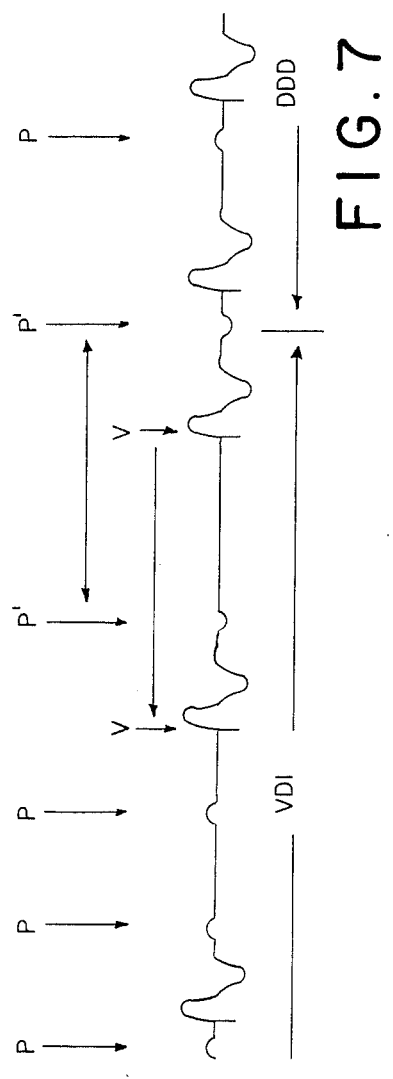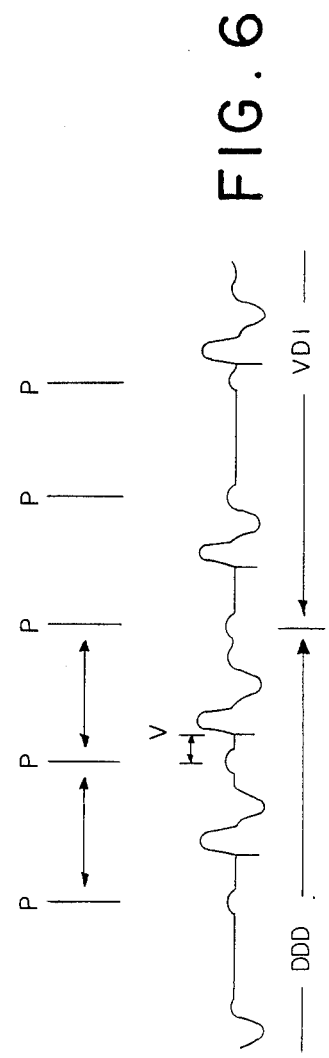
FIG. 7
FIG. 6

DUAL CHAMBER RATE RESPONSIVE PACEMAKER

BACKGROUND OF THE INVENTION

1. Field of the Invention

The present invention relates to cardiac pacemakers and more particularly to pacemakers which combine sensor based, rate determining algorithms with atrial synchronized pacing.

2. Description of the Prior Art

The first pacemakers operated asynchronously with respect to the patient's underlying heartbeat. These VOO mode pacemakers are typified by U.S. Pat. No. 3,057,356 to Greatbatch. Although the VOO pacing modality was sufficient to sustain life, the occasional competition between the pacing stimulus and the natural heartbeat of the patient was considered undesirable.

In response, the VVI mode, or ventricular inhibited pacing modality, as typified by U.S. Pat. No. 3,345,990 to Berkovits, was introduced. This modality eliminates competitive pacing with naturally occurring ventricular rhythms. This type of pacemaker provides a sense amplifier to detect the ventricular beat of the patient's heart. The detection of a ventricular beat inhibits the generation of a ventricular stimulus. The detected beat also resynchronizes the pacemaker by recycling or restarting the V-V escape interval timer. This synchronized behavior causes the VVI pacer to fill in missed beats on demand.

The atrial synchronized pacing modalities, such as the VAT mode typified by U.S. Pat. No. 3,254,596 to Keller, provide an atrial sense amplifier for detecting atrial depolarizations of the patient's heart. In these pacers, the atrial event initiates an A-V delay timer which will provoke a ventricular pace event if a naturally conducted ventricular beat does not follow the spontaneous atrial beat. These pacemakers provide the hemodynamic benefits of A-V synchrony along with the ability to follow or track the naturally occurring atrial rate of the patient.

The benefits of A-V synchrony are also provided by the DVI mode pacemaker which operates on the A-V sequential principle. This device is typified by U.S. Pat. No. 3,595,242 to Berkovits. This form of pacemaker provides stimulation in both the atrium and the ventricle while providing for ventricular sensing and synchronization. In this form of pacemaker, a ventricular sense event initiates a V-A timer as well as a V-V timer. At the expiration of the V-A interval, the pacemaker provides a stimulus to the atrium. In a similar fashion at the expiration of the V-V time interval, the pacemaker will provide a ventricular stimulus to the patient's heart. Each of these events will occur unless during the concurrent V-A and V-V time interval there is a sensed ventricular beat which will recycle or restart both timers. Therefore this pacer does not compete with ventricular rhythms but may compete in the atrium. In the DDI mode pacer, typified by U.S. Pat. No. 3,747,604 to Berkovits, there is also included an atrial sense amplifier for inhibiting the generation of the atrial pacing stimulus at the conclusion of the V-A interval, if a natural atrial depolarization occurs within that V-A time interval. This pacing modality also incorporates a V-V timer and provides both ventricular and atrial pacing to restore A-V synchrony while preventing both atrial and ventricular competition.

The DDD pacemaker is typified by U.S. Pat. No. 4,312,355 to Funke and shares many of the characteristics of the DVI and DDI pacers but in addition permits the synchronization of the pacemaker upon the atrial rate. The DDD pacer provides both an A-V timer and a V-A timer. In operation, the V-A timer is started upon the occurrence of a ventricular event, either sense or pace, and the A-V timer is started upon either atrial sense or pace. At the conclusion of the respective time intervals, atrial and ventricular stimuli are delivered to the heart if required.

All of the atrial synchronized pacemakers discussed above track the patient's underlying atrial rate when it is appropriate. However, each of these devices must provide mechanisms to prevent tracking atrial rates at high rates which are pathologic. Likewise, these pacemakers must provide a backup or standby pacing rate in the absence of detected atrial activity.

The upper rate characteristic of atrial synchronized pacemakers has been the subject of much study and debate. See, for example, "Dual Chamber Pacemakers: Upper Rate Behavior", PACE, Vol. 8, March/April 1985.

The upper rate characteristic of the pacer of the present invention is related to the autodecremental upper rate behavior set forth in "Improved DDD Pacing with a New Rate-Limiting Algorithm" by Barouh V. Berkovits published in the *Proceedings of the VIIIth World Symposium on Cardiac Pacing and Electrophysiology*. This paper discusses an upper rate limiting algorithm in which the pacemaker leaves an atrial synchronized pacing modality when the atrial rate exceeds the upper rate limit and begins to pace in a rate decrementing VDI mode. This VDI mode is similar to the VVI mode, but atrial activity is monitored as well as ventricular activity.

Also important to an understanding of the present invention is an awareness of the rapidly advancing rate responsive pacing modalities.

Implantable sensors and transducers which permit estimation of a body's demand for oxygenated blood have become available and have been incorporated into pacemakers to control the pacing rate. Many variables have been monitored to estimate the patient's metabolic demand. One such pacer which monitors patient activity is shown by U.S. Pat. No. 4,428,378 to Anderson and Brumwell. Another pacer which monitors the patient's minute ventilation is shown in U.S. Pat. No. 4,596,251 to Plicchi and Canducci.

The atrial depolarization rate of the heart, however, is still regarded by many investigators as the best indicator for setting a pacing rate, and as a consequence, many investigators have attempted to combine an atrial synchronized or P-wave sensing pacemaker with sensor or transducer based pacing rate. One such effort has been disclosed in U.S. Pat. application ser. no. 125,422 filed Nov. 25, 1987. This DDD device has essentially two escape interval timers. The first timer is a V-A timer with a value selected by the physician to set a lower rate limit. The second timer is an activity modulated V-A timer reflecting the patient's activity level.

In operation, such a device paces at the first to expire V-A time. This operational sequence provides sensor based atrial pacing above a physician selected rate floor.

However, consider the case in which the patient is experiencing a pathologically high atrial rate. The atrial tracking behavior causes the ventricular rate to accelerate to the ventricular rate pacing limit while ignoring the sensor output which may indicate a more physiologic rate.

Such devices ignore the sensor output at high atrial rate and Wenckebach.

SUMMARY OF THE INVENTION

In contrast to this prior art, the pacer of the present invention prefers to follow the atrium over a physiologically normal range and only paces based upon the sensor output if the atrial rate is pathologically high or low. This behavior is achieved by discontinuing atrial synchronized pacing when the atrial rate is above the upper rate limit. In this case ventricular pacing is controlled by a transition rate algorithm which moves the ventricular pacing rate to the sensor based rate. The rate decrementing transition algorithm is invoked only when the sensed atrial rate is above a physiologic range. For example, when the sensed atrial rate is within a normal range defined by the upper and lower rate limits, the pacer tracks the atrium in a DDD mode.

However, when the sensed atrial rate exceeds the programmable upper rate limit, the transition rate algorithm is invoked, and the pacemaker enters a VDIR ventricular pacing modality. In this mode, the pacer no longer synchronizes ventricular stimulation upon the sensed atrial signal, nor does the pacer provide stimulation to the atrium. Under these conditions, the ventricular escape interval of the pacemaker is gradually lengthened to produce a smooth rate fallback to provide a transition from the atrial rate to the lower sensor rate. If the atrial rate remains abnormally high, the pacemaker will eventually fall back to the sensor controlled ventricular pacing rate.

However, whenever the atrial rate drops below the programmed upper rate, the pacer begins to decrease the ventricular escape interval providing a gradually increasing pacing rate which will cause the ventricular pacing rate to converge toward atrial sense rate. Under these conditions, a rate incrementing transitional algorithm will continue until the point where the ventricular pacing rate equals the sensed atrial rate. At this point, the pacemaker leaves the ventricular inhibited VDIR pacing modality and re-enters the atrial synchronized DDD pacing mode. Thus the transition rate algorithm prevents abrupt rate changes when transferring from the sensor or to the atria.

In the case where the atrial signal is absent or the atrial rate is pathologically low, the pacer will pace the heart at a sensor based rate in a DDDR mode where the sensor controls both the atrial and ventricular esape intervals, thus prevents bradycardia and prevents A-V synchrony.

BRIEF DESCRIPTION OF THE DRAWINGS

FIG. 4 is a schematic surface electrogram depicting the operation of the pacer in response to premature atrial contractions;

FIG. 5 is a schematic surface electrogram depicting the operation of the pacer in response to premature atrial contractions;

FIG. 6 is a schematic surface electrogram depicting the DDD to VDIR mode transition; and FIG. 7 is a schematic surface electrogram depicting the VDIR to DDD mode transition.

DESCRIPTION OF THE PREFERRED EMBODIMENT

Hardware suitable for practicing the present invention includes the Medtronic Dysrhythmia Research Instrument which is available from Medtronic, Inc., Fridley, Minnesota. This machine is a computer based physiologic stimulator operating under the control of software. The computer hardware is interfaced with the heart through atrial and ventricular sense amplifiers and an atrial and ventricular pulse generators. U.S. Pat. No. 4,577,633, which is incorporated by reference, describes this computer driven stimulator in more detail.

An additional interface must be added to permit the integration of a sensor for the estimation of metabolic demand by the patient. A suitable sensor is disclosed in U.S. Pat. No. 4,428,378 to Anderson and Brumwell, which sets forth structure for monitoring physical activity of the body to set a pacing rate. This patent is also incorporated by reference.

The operation function and structure of the present invention will be set forth topically in connection with the rate diagrams and schematic EKG diagrams; then the software underlying the operation and function will be described in connection with the flowchart.

Rate Response

The pacemaker's ventricular stimulation rate may be set in accordance with one of three methods or ways.

Figure 1:
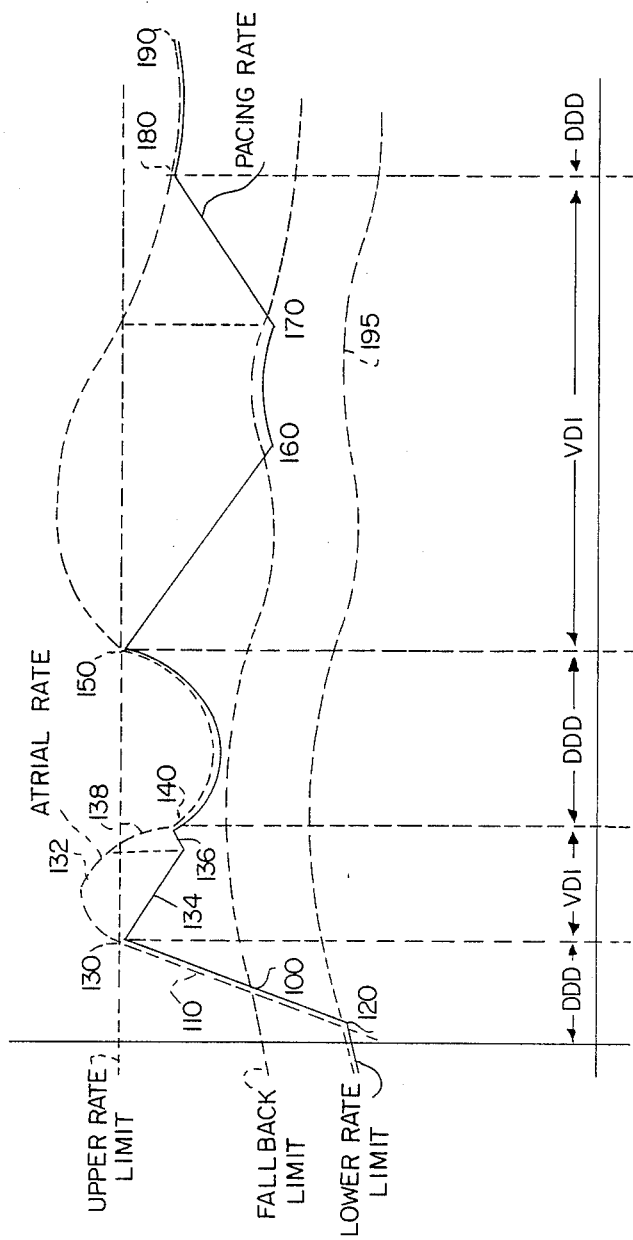
FIG. 1 is a rate diagram for the pacer of the invention.
Figure 2:
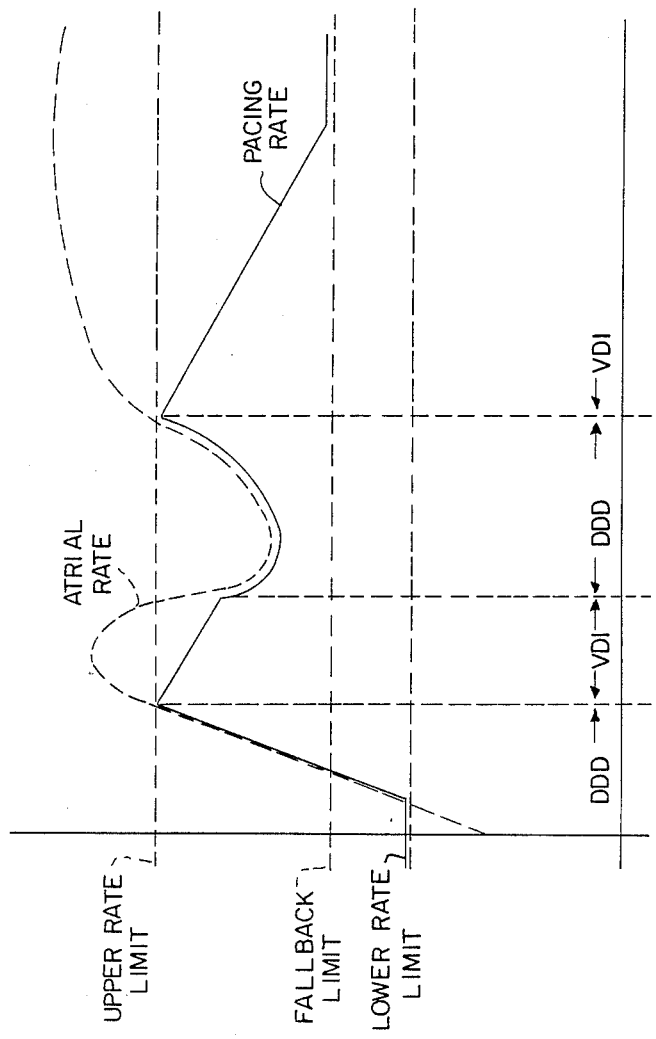
FIG. 2 is a rate diagram for a closely related prior art pacer.

The first way is depicted on the segment labelled DDD on FIG. 1. As shown on the figure, the pacer's ventricular stimulation rate shown as solid line 100 is dictated by the sensed atrial rate shown as dotted line 110. This behavior is shown between inflection points 120 to 130, 140 to 150 and 180 to 190 and corresponds to conventional DDD pacing. This behavior occurs when the atrial rate is within a physiologic range defined by the programmed upper rate limit 105 and the sensor controlled lower rate limit 195.

The second way is depicted in the segments labelled VDIR on FIG. 1. When the atrial rate exceeds the programmed upper rate, the ventricular rate is dictated by an transition rate algorithm. As the atrial rate goes above the limit as shown at 132, the ventricular stimulation rate falls back or decreases as shown at 134. If the atrial rate subsequently drops below the programmed upper rate limit 138, then the ventricular stimulation rate increases 136 until the atrial sensed rate is equal to the ventricular stimulation rate. Thus when the sensed P-P interval of the pacer is outside the physiologic range defined by rate limits 195 and 105, the device ceases to pace the atrium and paces in the ventricle at a rate dictated by the transition rate algorithm.

However, when the sensed P-P interval returns to the physiological limits shown at 195 and 105, the transition rate algorithm gradually alters the V-V interval to converge the V-V interval or paced rate to the sensed P-P interval or sensed rate. At the point where the sensed and paced rate are the same as shown at 140, the pacer switches from the adaptive rate algorithm to the atrial synchronized, DDD pacing mode.

The third way is depicted on FIG. 1 by segment 160 to 170. When the ventricular rate dictated by the transition rate algorithm is equal to or below the ventricular rate called for by the physiologic sensor, the pacer switches from the adaptive rate algorithm to the sensor based algorithm.

There is also a lower rate limit below which the heart will be stimulated in the absence of naturally occurring heart signals. This lower rate limit may be a fixed value or may be set as a function of the sensor as shown at 195.

In summary, the ventricular pacing rate may be dictated by the atrium when the atrial rate is appropriate, and both the atrial and the ventricular pacing rate may be dictated by the sensor when the atrial rate is inappropriate.

These two physiologic rate determining methods are connected and complimented by the transition rate algorithm which serves to smooth the transition between the sensor rate and the atrial rate.

Each of the methods of setting the rate will be discussed individually, and then the transitions between the modes will be discussed.

DDD—While operating in the DDD mode, the pacemaker is capable of pacing in both the atrium and ventricle and causes the ventricular pacing rate to track the atrial sensing rate. Each atrial sense event initiates an A-V delay timer which generates a ventricular pace event at the conclusion of the A-V time. In a similar fashion, a ventricular sense event will start a V-A timer which will generate an atrial pace event at the conclusion of the V-A time interval.

During the A-V time interval, if a ventricular event is sensed by the pacemaker, it inhibits or cancels the otherwise scheduled ventricular pace event and starts the V-A timer.

If an atrial event is detected during the V-A time interval, the pacemaker cancels the otherwise scheduled atrial pace event and immediately initiates an A-V time interval.

As a consequence, the DDD pacemaker can synchronize on both atrial and ventricular activity and will track atrial activity. This pacing behavior is the preferred atrial synchronous modality for the present invention; however, there are numerous variations on the DDD modality, and other atrial synchronized behaviors may be suitable for use in this invention as well.

In operation, in the DDD mode, the pacemaker is capable of stimulating in both the atria and ventricle. The tracking behavior is shown on FIG. 1 between the inflection points 120 and 130 on the rate diagram where the ventricular rate is synchronized to the sensed atrial rate.

VDIR—If the atrial rate exceeds a programmed upper rate limit as indicated by sensed P-P intervals shorter than the programmed ventricular rate limit, the pacemaker will no longer synchronize on the atrial activity, and all atrial pacing ceases. The ventricular escape interval of the pacemaker will be gradually incremented through an adaptive transition rate algorithm which may add a fixed increment to the escape interval to permit the ventricular rate to fall back or slow down. This behavior reflects the assumption that atrial rates above the programmed upper rate limit no longer indicate the body's physiologic demand for oxygenated blood but rather indicate an arrhythmia.

This gradual rate fallback characteristic is desired to prevent an abrupt change in ventricular pacing rate which causes discomfort to the patient. This gradual lengthening of the ventricular escape interval continues until one of two events takes place.

In the first case, if the atrial rate drops below the programmed upper rate limit, then the ventricular escape interval will be gradually shortened rather than lengthened to promote the convergence of the ventricular pacing rate with the atrial sensing rate.

The second possibility is the gradual fallback to the a sensor controlled escape interval which reflects the sensor-based estimate of the appropriate pacing rate. This occurs when the sensor rate escape interval is shorter than the fallback interval.

At this instant, the sensor takes over pacing rate control and continues to control it until the atrial rate drops below the upper rate limit.

At this moment, the transition algorithm will be the shorter escape interval of the pacemaker until the ventricular pacing rate equals the atrial sensing rate.

At the present time, a preferred sensor is one which monitors physical activity if the body is set forth in U.S. Pat. No. 4,428,378. Other sensor-based rates may also prove useful in this connection.

While the device is operating in the VDIR modality, only the ventricle is being stimulated; however both atrial and ventricular sensing are maintained. The ventricular sensing is used to avoid competition in the ventricle by inhibiting and synchronizing the pacemaker upon any naturally occurring ventricular beats which occur. Atrial sensing is maintained to compute the P-P interval to control the rate transition algorithm and the mode switching of the pacemaker.

Upper Rate Behavior—Pacers which are atrial synchronized may exhibit pacemaker meditated tachycardia (PMT). The two prerequisites for such endless loop tachycardias are retrograde conduction and P-wave triggering. This PMT phenomenon occurs when a ventricular stimulus is conducted in the retrograde direction up the A-V pathways and stimulates the atria. The resulting atrial depolarization initiates another ventricular stimulus after a brief A-V delay which may result in a rapid ventricular stimulation rate.

It has been conventional to provide a Wenckebach response in the presence of high atrial rates. Such a response is characterized by a gradual prolongation of the observed A-V interval. This prolongation of the A-V interval facilitates the retrograde conduction and thus supports the endless loop tachycardias. Since the Wenckebach response provides both the requisite of the PMT, it is not the optimum upper rate behavior.

The present pacer addresses these issues by providing a different rate limiting algorithm which differentiates between premature atrial beats (PAC) and atrial tachycardia. The pacer minimizes the potential for retrograde conduction by shortening the A-V interval after a premature beat and also interrupts atrial triggering when the atrial rate is too fast. These characteristics alleviate the need for long atrial refractory periods which are undesirable because they limit the tracking ability of the pacer. Also these characteristics prevent fast ventricular pacing as a result of atrial tachyarrhythmias.

The pacer defines a PAC as two consecutive atrial sense events which exhibit a P-P interval less than a physician programmed amount. An atrial tachycardia is defined by the pacer as two or more short P-P intervals.

Upon the occurrence of a PAC, the pacer stimulates the ventricle if required at the conclusion of a shortened A-V delay interval.

One consequence of atrial tracking, especially at high rates, is the risk of providing a ventricular stimulus while the ventricle itself is repolarizing. If the stimulus occurs during the vulnerable phase of the repolarization, a lethal arrhythmia could be induced.

In the present pacer, such a stimulus is precluded by an R-V timer. This timer is implemented in software and prevents the delivery of a ventricular stimulus until the expiration of 250ms since the last ventricular sense event.

This time interval is programmable and should be long enough to overlap the T wave segment of ventricular repolarization.

An electrographic representation of this behavior is shown in FIG. 4 where P wave 410 occurs shortly after P wave 400 and therefore calls for a short (100 ms) A-V delay period. However, the scheduled ventricular stimulus is delayed until the expiration of a 250 ms R-V delay period and therefore occurs with an observed A-V delay time of 180 ms as shown on the figure.

The operation of this intervention is depicted in connection with FIGS. 4 and 5. In FIG. 4, the naturally occurring P-wave 400 is followed 200 ms later by another atrial beat. This beat meets the prematurity criteria and is labelled as a premature atrial contraction 410 on the diagram. Based upon the programming of the device, a ventricular stimulus should follow after the atrial contraction at the conclusion of a 100 ms A-V delay interval. However, the expiration of the A-V delay interval would call for a ventricular stimulus only 170 ms after the last ventricular depolarization labelled 420 on the diagram. Since this scheduled ventricular stimulus falls within the 250 ms programmed R-V interval, pacing is prohibited until the expiration of that interval expires. This results in an observed A-V delay interval of 180 ms.

Thus, as shown in the drawing, ventricular pacing which is called for by the end of an A-V delay interval during the R-V interval results in a ventricular stimulus delivered synchronously with the conclusion of the R-V interval. This behavior may be contrasted to the behavior shown in FIG. 5 where the premature atrial contraction 540 is followed by a short A-V interval of 100 ms resulting in a ventricular stimulus 550 since the ventricular stimulus falls outside of a 250 ms R-V protection period.

It is preferred that this shortened A-V interval be independently programmable to a value equal to or less than the normal A-V delay period selected by the physician.

The objective of this behavior is to protect against A-V prolongation after early atrial beats while maintaining the atrial tracking aspect of the DDD modality.

In response to two short P-P intervals, the pacer switches its pacing modality from DDD to a ventricular stimulating regime without atrial tracking. This has been labelled throughout the drawings as a VDIR mode. In this modality, the atrial rate is monitored, but it is not used to synchronize the ventricular stimulus. An example of this behavior is shown in FIG. 6 where the P-P interval of events 600 to 610 and 610 to 620 are sufficiently short to declare an atrial tachycardia. Consequently no ventricular stimulus is keyed to atrial event 620, et seq. The ventricular stimulus shown at 670 is the result of escape interval time out at the preceding R-R measured interval. The next escape will occur in accordance with the fallback algorithm.

Figure 3:
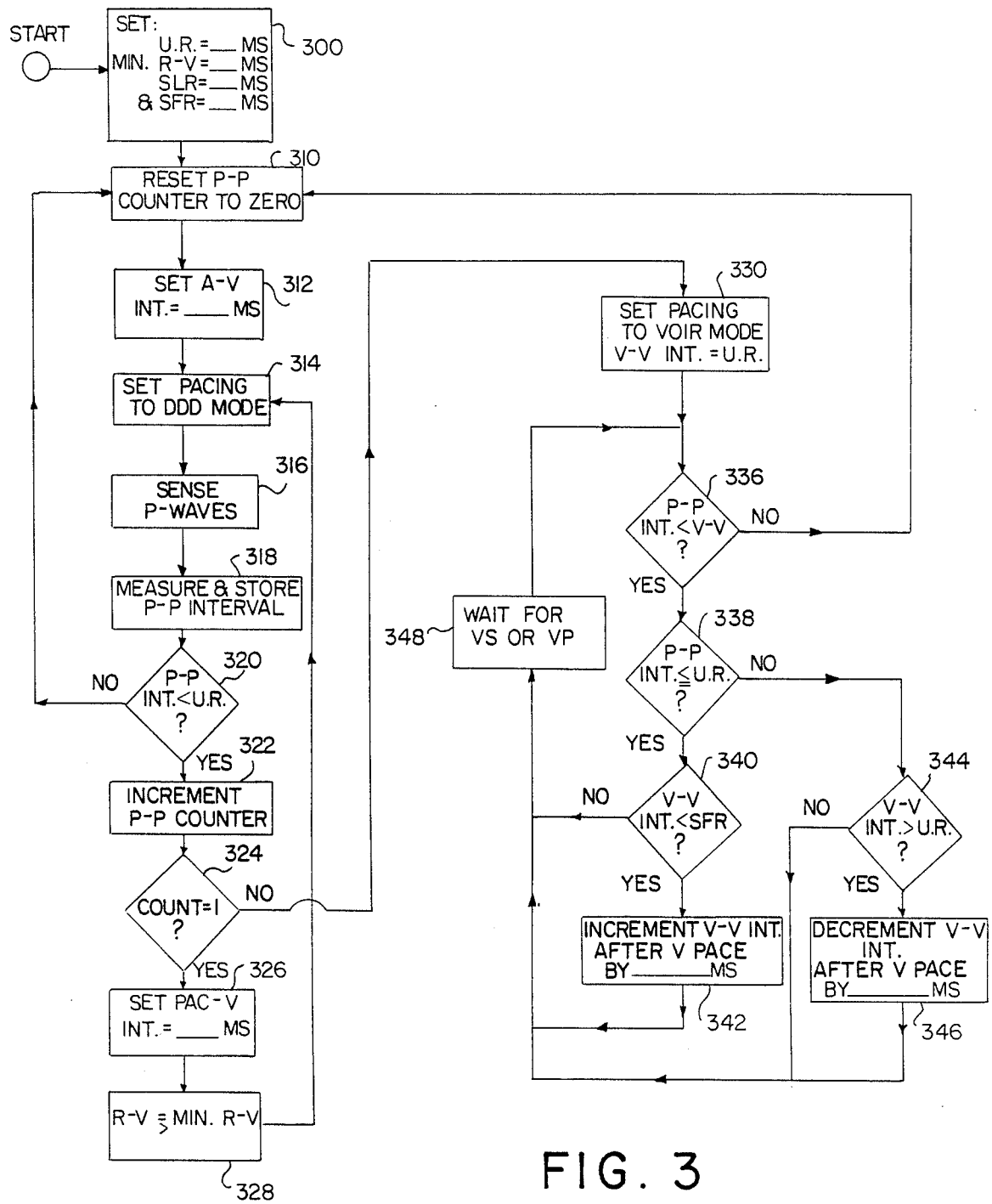
FIG. 3 is a software flowchart showing an exemplary method for carrying out the present invention.

Software—FIG. 3 is a flowchart depicting in schematic form the software for carrying out the present invention. Block 300 corresponds to the initialization routine. At this time the physician selected upper rate limit is established along with the selected R-V protection interval. The pacer also reads the sensor output to set an initial value for the sensor controlled fallback rate and the sensor controlled lower rate.

At block 310, the P-P counter which keeps track of the sensed atrial rate is reset to zero. It is this counter which controls the program flow to result in a shortened A-V stimulating period after a single PAC and results in a mode shift after two PAC's.

At block 312, the A-V delay timer value is set for the DDD modality.

At block 314, the pacemaker is configured in its atrial synchronized modality to provide both atrial and ventricular stimuli upon demand.

At block 316, the occurrence of a sensed atrial event is noted, and at 318 the interval between successive atrial events is measured.

The current atrial rate is compared with the physician programmed upper rate interval at block 320. If the atrial rate is within the physiologic bounds as discussed in connection with FIG. 1, the program returns to block 310 resetting the P-P counter to zero and proceeding with the DDD pacing regime.

If, however, the P-P interval is short either through the occurrence of a PAC or the onset of a tachyarrhythmia, the program falls through to block 322 where P-P counter is incremented. If this is the first PAC which has occurred, the pacemaker sets a shortened AV interval and returns to block 310.

The software flow is directed next to block 328 where the time interval between the last detected ventricular depolarization and the scheduled stimulus is evaluated. As described in connection with FIG. 4, ventricular stimulation is prohibited until a selected amount of time has elapsed since the last ventricular beat. This block permits the atrial synchronized ventricular pace to occur if the preset minimum R-V time has expired. The software flow then returns to block 314.

However if the counter of block 326 overflows indicating two PAC's, then the program flow is directed to block 330. This corresponds to an atrial rate above the rate limit.

At block 330, the pacer changes to the VDIR mode and sets the V-V escape interval to the value of the upper rate limit interval.

At block 336 the atrial rate (P-P) is evaluated and if the atrial rate is below the ventricular rate (V-V) the software flow directs the program to block 310 where atrial synchronized DDD pacing is restarted. If, however, the atrial rate is faster than the ventricular rate, the flow is directed to block 338. Here the atrial rate is compared to the upper rate interval.

At block 338 the atrial rate (P-P) is compared with the upper rate limit interval (VR). If the atrial rate is above the rate limit, the ventricular rate may be decreased via blocks 340, 342, 348. If the atrial rate is below rate limit, the ventricular rate may be sped up via block 344, 346, 348.

Turning to block 340, the current V-V escape interval is compared with the sensor based SFR interval. If the sensor rate is faster than the adaptive rate escape interval, the sensor rate governs. However, if the sensor rate is lower, the V-V interval is incremented at block 342 to gradually adapt the V-V interval to the sensor rate.

The alternate path from block 338 shown at 344 and 346 is invoked to speed up the V-V rate to converge it with a fast but acceptable atrial rate P-P.

What is claimed is:

1. A cardiac pacer for implantation in the body of a patient, comprising:
   atrial sensing means for detecting atrial depolarizations;
   means for defining an upper rate;
   monitoring means responsive to the detection of atrial depolarizations by said sensing means for determining the rate of said atrial depolarizations;
   ventricular pulse generating means for generating ventricular stimulus pulses;
   means responsive to detection of an atrial depolarization by said sensing means for triggering said ventricular pulse generating means to generate a stimulus pulse at a predetermined A-V interval thereafter;
   sensor means for estimating the demand of said patient's body for oxygenated blood;
   rate determining means responsive to said sensor means for defining a ventricular pacing rate based on the estimation of the demand of said patient's body for oxygenated blood by said sensor means; and
   mode switching means for switching said pacer between a first mode in which said responsive means is enabled to trigger said ventricular pulse generating means to generate ventricular stimulating pulses in response to and at said predetermined A-V interval after the detection of said atrial depolarizations by said sensing means and a second mode in which said responsive means is prevented from triggering said ventricular pulse generator in response to the detection of atrial depolarizations and in which said rate determining means triggers generation of ventricular stimulus pulses by said ventricular pulse generating means at said ventricular pacing rate, said mode switching means responsive to said monitoring means for switching from said first mode to said second mode in response to determination of a rate of atrial depolarizations which exceeds said upper rate, said mode switching means switching between said second mode and said first mode in response to said monitoring means measuring a rate of atrial depolarizations less than said upper rate, said atrial monitoring means operative to monitor the rate of said atrial depolarizations in both said first and second modes.

2. A pacer according to claim 1 wherein said mode switching means further comprises rate incrementing means operative while said pacer is in said second mode and activated in response to the detection of a rate of atrial depolarizations below said upper rate, by said monitoring means, said rate incrementing means triggering said ventricular pulse generating means at an increasing rate, said increasing transition rate gradually increasing from said ventricular rate defined by said rate determining means until equal to the rate of atrial depolarizations determined by said monitoring means, said mode switching means thereafter switching the operation of said pacer from said second mode to said first mode.

3. A pacemaker according to claim 1 or claim 2 wherein said mode switching means further comprises rate decrementing means activated in response to the detection of a rate of atrial depolarizations in excess of said upper rate, by said monitoring means, said rate decrementing means triggering said ventricular pulse generating means at a decreasing transition rate, said decreasing transition rate gradually decreasing from said upper rate to said ventricular rate defined by said rate determining means.

4. A cardiac pacer for implantation in the body of a patient, comprising:
   atrial sensing means for detecting the occurrence of atrial depolarizations;
   means for defining an upper rate;
   monitoring means for determining the rate of atrial depolarizations;
   ventricular pulse generating means for generating ventricular stimulus pulses;
   means responsive to the detection of an atrial depolarization by said sensing means for triggering said ventricular pulse generating means to generate a ventricular stimulus pulse at a predetermined A-V interval thereafter;
   fallback rate defining means for defining a ventricular pacing fallback rate lower than said upper rate; and
   mode switching means for switching the operation of said pacer between a first mode in which said responsive means triggers generation of a ventricular stimulus pulse by said ventricular pulse generating means in response to and at said predetermined A-V interval after the detection of an atrial depolarization by said sensing means and a second mode in which said responsive means is prevented from triggering generation of ventricular stimulus pulses and in which said fallback rate defining means triggers said ventricular pulse generating means to generate ventricular stimulus pulses at said fallback rate, said mode switching means operative to switch the operation of said pacer from said first mode to said second mode in response to the detection of a rate of atrial depolarizations in excess of said upper rate, by said monitoring means, and switching the operation of said pacer from said second mode to said first mode in response to the detection of a rate of atrial depolarizations less than said upper rate, by said monitoring means, said monitoring means further comprising rate incrementing means activated when said pacemaker is in said second mode, and in response to the detection of a rate of atrial depolarizations less than said upper rate by said monitoring means, said rate incrementing means defining an increasing transition rate, said increasing transition rate gradually increasing from said fallback rate defined by said fallback rate defining means until equal to the rate of atrial depolarizations determined by said monitoring means, said mode switching means thereafter operative to switch the operation of said pacer from said second mode to said first mode.

5. A pacemaker according to claim 4 further comprising rate decrementing means, said rate decrementing means activated in response to the detection of a rate of atrial depolarizations in excess of said upper rate by said monitoring means, said rate decrementing means triggering said ventricular pulse generating means at a decreasing transition rate, said decreasing transition rate gradually decreasing from said upper rate to said fallback rate.

* * * * *